(12) United States Patent
Beer

(10) Patent No.: US 8,189,186 B2
(45) Date of Patent: May 29, 2012

(54) SIGNAL ENHANCEMENT USING A SWITCHABLE MAGNETIC TRAP

(75) Inventor: Neil Reginald Beer, Pleasanton, CA (US)

(73) Assignee: Lawrence Livermore National Security, LLC., Livermore, CA (US)

( * ) Notice: Subject to any disclaimer, the term of this patent is extended or adjusted under 35 U.S.C. 154(b) by 1137 days.

(21) Appl. No.: 11/965,598

(22) Filed: Dec. 27, 2007

(65) Prior Publication Data

US 2011/0215798 A1    Sep. 8, 2011

(51) Int. Cl.
*G01N 21/04* (2006.01)
(52) U.S. Cl. ......................................... 356/244; 436/526
(58) Field of Classification Search .................. 436/526; 356/244, 246
See application file for complete search history.

(56) References Cited

U.S. PATENT DOCUMENTS

| | | | |
|---|---|---|---|
| 2002/0127740 A1* | 9/2002 | Ho | 436/518 |
| 2002/0172969 A1 | 11/2002 | Burns et al. | |
| 2004/0007463 A1 | 1/2004 | Ramsey et al. | |
| 2005/0019902 A1 | 1/2005 | Mathies et al. | |
| 2005/0042639 A1 | 2/2005 | Knapp et al. | |
| 2005/0048581 A1 | 3/2005 | Chiu et al. | |
| 2005/0130173 A1 | 6/2005 | Leamon et al. | |
| 2005/0221373 A1 | 10/2005 | Enzelberger et al. | |
| 2007/0243634 A1* | 10/2007 | Pamula et al. | 436/518 |

OTHER PUBLICATIONS

Yung-Chieh Tan, et al, "Monodispersed microfluidic droplet generation by shear focusing microfluidic device", Sensors and Actuators B 114 (2006) 350-356.
N. Reginald Beer, et al, "On-Chip, Real-Time, Single-Copy Polymerase Chain Reaction in Picoliter Droplets," Analytical Chemistry 2007, 79, 8471-8475.
N. Reginald Beer, et al, "New system detects small samples for big gains," Newsline, vol. 32, No. 39, Nov. 16, 2007.

* cited by examiner

*Primary Examiner* — Layla Lauchman
(74) *Attorney, Agent, or Firm* — Eddie E. Scott

(57) ABSTRACT

A system for analyzing a sample including providing a microchannel flow channel; associating the sample with magnetic nanoparticles or magnetic polystyrene-coated beads; moving the sample with said magnetic nanoparticles or magnetic polystyrene-coated beads in the microchannel flow channel; holding the sample with the magnetic nanoparticles or magnetic polystyrene-coated beads in a magnetic trap in the microchannel flow channel; and analyzing the sample obtaining an enhanced analysis signal. An apparatus for analysis of a sample includes magnetic particles connected to the sample, a microchip, a flow channel in the microchip, a source of carrier fluid connected to the flow channel for moving the sample in the flow channel, an electromagnet trap connected to the flow line for selectively magnetically trapping the sample and the magnetic particles, and an analyzer for analyzing the sample.

27 Claims, 4 Drawing Sheets

SIGNAL ENHANCEMENT USING A SWITCHABLE MAGNETIC TRAP

The United States Government has rights in this invention pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present invention relates to analysis of nucleic acids and more particularly to analysis of nucleic acids using signal enhancement with a switchable magnetic trap.

2. State of Technology

Microfluidic devices are poised to revolutionize environmental, chemical, biological, medical, and pharmaceutical detectors and diagnostics. "Microfluidic devices" loosely describes the new generation of instruments that mix, react, count, fractionate, detect, and characterize complex gaseous or liquid-solvated samples in a micro-optical-electro-mechanical system (MOEMS) circuit manufactured through standard semiconductor lithography techniques. These techniques allow mass production at low cost as compared to previous benchtop hardware. The applications for MOEMS devices are numerous, and as diverse as they are complex.

As sample volumes decrease, reagent costs plummet, reactions proceed faster and more efficiently, and device customization is more easily realized. By reducing the reaction volume, detection of target molecules occurs faster through improved sensor signal to noise ratio over large, cumbersome systems. However, current MOEMS fluidic systems may only be scratching the surface of their true performance limits as new techniques multiply their sensitivity by ten, a hundred, or even a thousand times.

The present invention provides a system for enhancing a microfluidic detector's limits by magnetically focusing the target analytes to be detected in an optical convergence zone until interrogation has been performed. The present invention provides an additional reduction of costly reagent volumes over standard MOEMS systems, since much fewer targeted reactions are needed to produce a detectable signal. This not only provides the desirable cost incentive, but can cut processing times by an order of magnitude, making many popular on-chip process, such as Polymerase Chain Reaction (PCR) truly real time.

The present invention provides a method for performing sample wash steps in-line to cleanse the sample of unwanted reaction by-products, change the buffered pH, introduce new or next-step reagents, and remove excess or previous-step reagents from the reaction and detection zones. This opens the door to multi-step sequential reactions occurring while the target molecules or complexes are held within detection and imaging zone.

The present invention has many uses in different technology fields. For example, the present invention has use in the following situations: Biowarfare detection applications: identifying, detecting, and monitoring bio-threat agents that contain nucleic acid signatures, such as spores, bacteria, and viruses; Biomedical applications: Tracking, identifying, and monitoring outbreaks of infectious disease including emerging, previously unidentified and genetically engineered pathogens; Automated processing, amplification, and detection of host or microbial and viral DNA or RNA in biological fluids for medical purposes; Automated processing and detection of proteomic signatures in biological fluids; Cell cytometry or viral cytometry in fluids drawn from clinical or veterinary patients for subsequent analysis; and High throughput genetic screening for drug discovery and novel therapeutics; Forensic applications: Automated processing, amplification, and detection DNA in biological fluids for forensic purposes; and Food and Beverage Safety: Automated food testing for bacterial or viral contamination.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system that provides up to a thousand fold signal enhancement for optical detection of bacterial cells, virus particles, nucleic acids, proteins, biomolecules, chemical agents, explosives agents, and other targets of interest in a micro-opto-electromechanical systems (MOEMS) device. The present invention provides a method for performing in-line sample focusing of target analytes, whether in continuous flow, slug flow, or partitioned in emulsion microreactors, for subsequent optical detection at greatly reduced times compared to other methods. The present invention provides also provides a method for performing in-line sample washing and buffering for complex reactions, and a real-time method for enhancing fluorescence detection through pH optimization.

Optical detection employs fluorescent probes which emit light when an electron which has been previously excited to an energy level above the ground state then gives off a photon to transition back to the ground state. For this process to occur in a solution, the pH of the solvent is critical as it affects the ability of the outer shell electrons in the probe molecule to efficiently transition between states. The present invention utilizes magnetic focusing as the solvent stream buffer is changed allows the real-time determination of the optimal buffer pH as well as the ability to run the reaction at one pH and the subsequent detection at another, thereby utilizing different pH's at each step so both can be optimized.

The present invention provides a method of analyzing a sample including the steps of providing a microchannel flow channel; associating the sample with magnetic nanoparticles or magnetic polystyrene-coated beads; moving the sample with said magnetic nanoparticles or magnetic polystyrene-coated beads in the microchannel flow channel; holding the sample with said magnetic nanoparticles or magnetic polystyrene-coated beads in a magnetic trap in the microchannel flow channel; and analyzing the sample obtaining an enhanced analysis signal. Another embodiment of the method includes the step of holding the sample with the magnetic nanoparticles or magnetic polystyrene-coated beads in the magnetic trap in the microchannel flow channel while washing the sample or exposing the sample to reagents or exposing the sample to other conditions.

The present invention provides an apparatus for analysis of a sample, including magnetic particles connected to the sample, a microchip, a flow channel in the microchip, a source of carrier fluid connected to the flow channel for moving the sample in the flow channel, an electromagnet trap connected to the flow line for selectively magnetically trapping the sample and the magnetic particles, and an analyzer for analyzing the sample. The present invention also provides a method of analyzing a sample on a microchip, including the steps of providing a microchannel flow channel in the microchip; associating the sample with magnetic nanoparticles or magnetic polystyrene-coated beads; moving the sample with the magnetic nanoparticles or magnetic polystyrene-coated beads in the microchannel flow channel, trapping the sample with the magnetic nanoparticles or magnetic polystyrene-coated beads in a magnetic trap in the microchannel flow channel, and analyzing the sample.

The present invention has many uses in different technology fields. For example, the present invention has use in the following situations: Biowarfare detection applications: identifying, detecting, and monitoring bio-threat agents that contain nucleic acid signatures, such as spores, bacteria, and viruses; Biomedical applications: Tracking, identifying, and monitoring outbreaks of infectious disease including emerging, previously unidentified and genetically engineered pathogens; Automated processing, amplification, and detection of host or microbial and viral DNA or RNA in biological fluids for medical purposes; Automated processing and detection of proteomic signatures in biological fluids; Cell cytometry or viral cytometry in fluids drawn from clinical or veterinary patients for subsequent analysis; and High throughput genetic screening for drug discovery and novel therapeutics; Forensic applications: Automated processing, amplification, and detection DNA in biological fluids for forensic purposes; and Food and Beverage Safety: Automated food testing for bacterial or viral contamination.

Systems constructed in accordance with the present invention provide unexpected and improved results. The article "On-Chip, Real-Time, Single-Copy Polymerase Chain Reaction in Picoliter Droplets," by N. Reginald Beer, Benjamin J. Hindson, Elizabeth K. Wheeler, Sara B. Hall, Klint A. Rose, Ian M. Kennedy, and Bill W. Colston; in *Analytical Chemistry*, Vol. 79, No. 22: Nov. 15, 2007 shows that some portions or all of the systems were tested and analyzed. The article "New system detects small samples for big gains" in NewsLine, Vol. 32, No. 39, Nov. 16, 2007, also shows that some portions or all of the systems were tested and analyzed. The article "On-Chip, Real-Time, Single-Copy Polymerase Chain Reaction in Picoliter Droplets," by N. Reginald Beer, Benjamin J. Hindson, Elizabeth K. Wheeler, Sara B. Hall, Klint A. Rose, Ian M. Kennedy, and Bill W. Colston; in *Analytical Chemistry*, Vol. 79, No. 22: Nov. 15, 2007 and the article "New system detects small samples for big gains" in NewsLine, Vol. 32, No. 39, Nov. 16, 2007 are incorporated herein by this reference.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
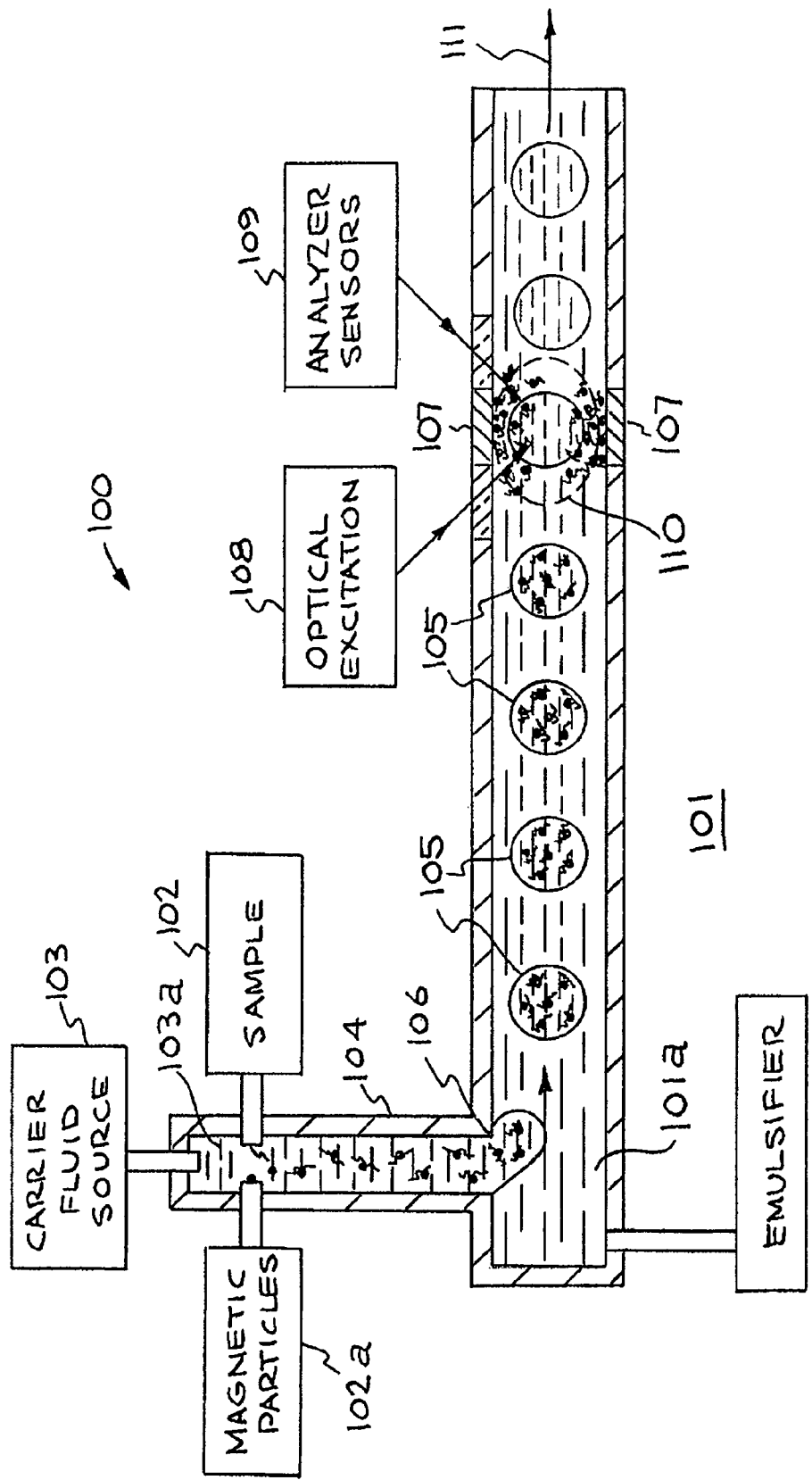
FIG. 1 illustrates one embodiment of a system for signal enhancement in optical detection of bacterial cells, virus particles, nucleic acids, proteins, biomolecules, chemical agents, explosives agents, and other targets of interest in a micro-opto-electromechanical systems (MOEMS) device.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Referring now to the drawings and in particular to FIG. 1, one embodiment of a system for analyzing a sample constructed in accordance with the present invention is illustrated. The system is designated generally by the reference numeral 100. The system 100 facilitates analyzing a sample on a microchip 101. The microchip 101 includes a microchannel flow channel 101a. A carrier fluid source 103 introduces a carrier fluid 103a through a connecting channel 104 into the flow channel 101a. The sample 102 to be analyzed together with associated magnetic particles 102a is introduced to the channel 104. The sample 102 can be bacterial cells, virus particles, nucleic acids, proteins, biomolecules, chemical agents, explosives agents, and other targets of interest.

A droplet maker 106 is connected to the channel 104 and flow channel 101a and produces droplets 105 containing the sample 102 and the magnetic particles 102a. The droplet maker 106 can be a "T" junction or other type of droplet maker. Another droplet make is disclosed in the article, "Monodispersed microfluidic droplet generation by shear focusing microfluidic device," by Yung-Chieh Tan, Vittorio Cristini and Abraham P. Lee, in *Sensors and Actuators*, B: Chemical, Volume 114, Issue 1, 30 Mar. 2006, Pages 350-35 the article, "Monodispersed microfluidic droplet generation by shear focusing microfluidic device," by Yung-Chieh Tan, Vittorio Cristini and Abraham P. Lee, in *Sensors and Actuators*, B: Chemical, Volume 114, Issue 1, 30 Mar. 2006, Pages 350-35 is incorporated herein by reference.

The flow channel 101a caries sample 102 to be analyzed together with associated magnetic particles 102a for example, the flow channel 101a can carry genomic viral, bacterial, plant, animal, or human nucleic acid hybridized to magnetic-cored nanoparticles 102a (or polystyrene beads). The microchannel flow channel 101a cross section aspect ratio, width and depth, is sized to prevent the sample 102 and magnetic nanoparticles 102a (or magnetic polystyrene-coated beads) from vertical stacking.

The droplets or microreactors 105 containing the sample 102 with magnetic particles 102a are carried to a capture zone 110 by the carrier fluid 103. The droplets or microreactors 105 containing the sample 102 with magnetic particles 102a are trapped in the capture zone 110 by activation of electromagnets 107. The drops (isolated mobile reactors) 105 with their suspended magnetic particles 102a are captured in the magnetic and fluidic trap (capture zone) 110 using the electro magnets 107.

An analyzer system provides analysis of the sample 102. The analyzer system provides optical excitation by LED, laser, or other means 108 that will elicit the strongest response, and the analyzer system will capture this signal at such sensors as a photodiode with trans-impedance amplifier, or an imaging array such as a CCD or CMOS imager 109. The empty droplets are directed out of the system as indicated by the arrow 111.

Sample washing and reagent replacement or refresh can be performed with this system 100. The target molecules 102, attached to the magnetic beads 102a and held in the detection zone 110, can be washed by the continuous flow of the channel 101a which, with upstream valving, can bring new and different reagents for multi-step reactions, or change the buffered pH to improve the optical efficiency of the fluorescing probe. For reagent sequencing, this system allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" 110 by electromagnetic attraction.

Referring again to FIG. 1, the operation of the system 100 will be described. Aqueous fluid 102 containing magnetic nanoparticles 102a is introduced into a cross-channel flow of oil (or other carrier fluid) carrier fluid 103. The carrier fluid 103 can be oil, Flourinet™, water, or other carrier fluid. Flourinet™ is a fluorocarbon-based fluid and is the trademarked brand name for electronics coolant liquids sold commercially by 3M. The reactions between the hybridized molecules on the magnetic nanoparticle 102a and the catalyzed and buffered reagents within the aqueous stream occur, powered by the addition of heat or light into the channel if necessary. When the droplets 105 pass through the optical enhancement, or "Capture Zone" 110, the electromagnets strip 113 the passing droplets 105 of their nanoparticles 102a, accumulating them first near the walls (close to the magnets 107) and then further and further into the free stream of the fluid flow. As the entire channel begins to fill, optical density reaches a practical maximum, and the nanoparticles 102a are excited by laser or LED light source 108 into fluorescence. As they fluoresce, their emission is read by a photodiode with amplification (such as a Trans-impedance amplifier), or an imaging system such as a CCD or CMOS array 109. After the measurement is taken, the magnets 107 are de-energized and the magnetic beads, or nanoparticles, wash away, clearing the channel for the next assay.

Alternate embodiments utilize the same method applied to aqueous flows under Poiseiulle (parabolic) profiles, electrophoretic flows, segmented slug flows (aqueous with gas pockets), and others. Each requires simply a tuning of the magnetic force applied to capture and hold the magnetic nanoparticles.

Other embodiment of the system 100 provide a method of analyzing a sample including the steps of providing a microchannel flow channel; associating the sample with magnetic nanoparticles or magnetic polystyrene-coated beads; moving the sample with said magnetic nanoparticles or magnetic polystyrene-coated beads in the microchannel flow channel; holding the sample with said magnetic nanoparticles or magnetic polystyrene-coated beads in a magnetic trap in the microchannel flow channel; and analyzing the sample obtaining an enhanced analysis signal. An embodiment of the method includes the step of holding the sample with the magnetic nanoparticles or magnetic polystyrene-coated beads in the magnetic trap in the microchannel flow channel while washing the sample or exposing the sample to reagents or exposing the sample to other conditions.

Figure 2:
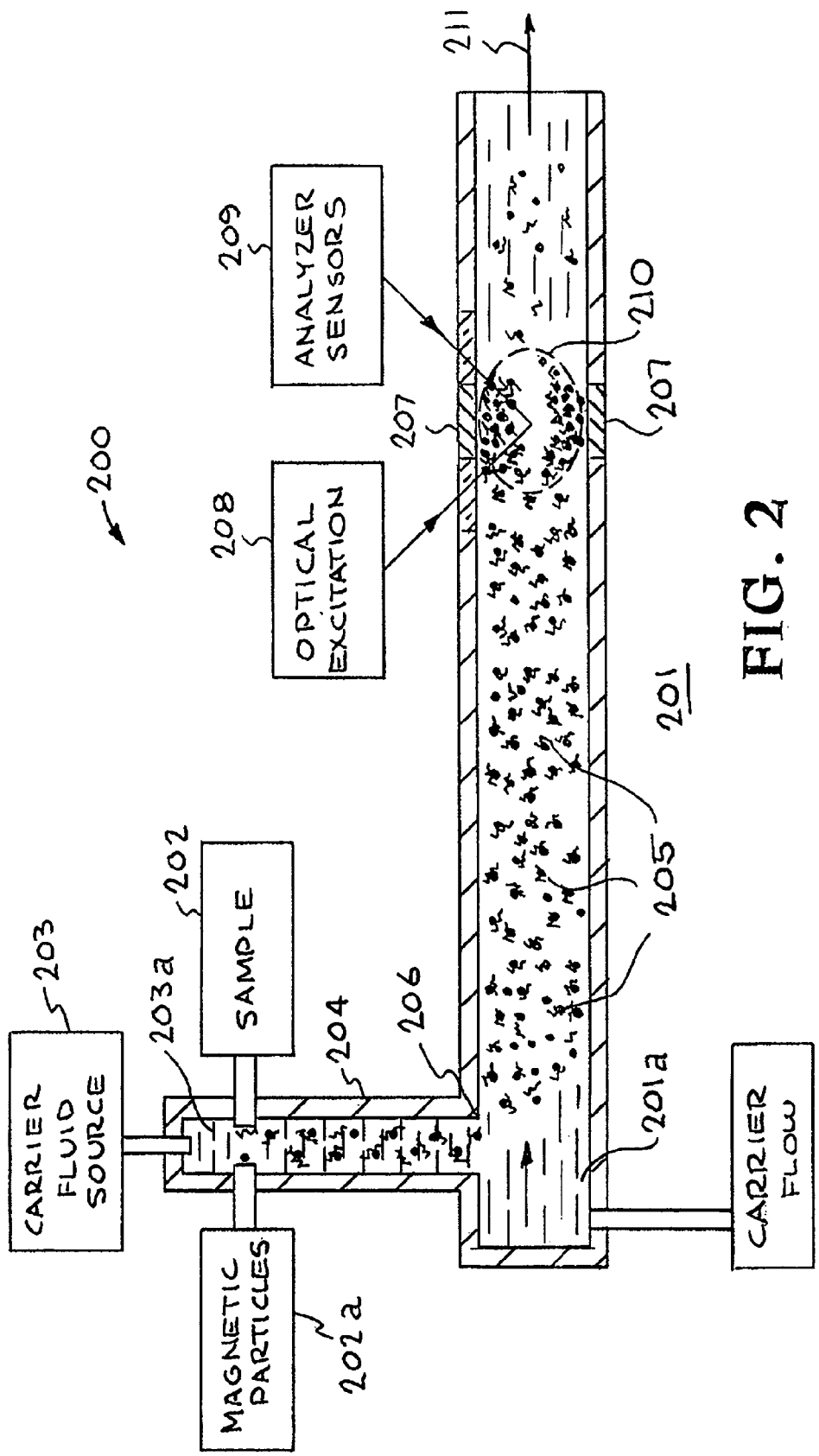
FIG. 2 illustrates another embodiment of a system for analyzing a sample constructed in accordance with the present invention.

Referring now to FIG. 2, another embodiment of a system for analyzing a sample constructed in accordance with the present invention is illustrated. The system is designated generally by the reference numeral 200. The system 200 provides analysis of a sample 202 on a microchip 201. The microchip 201 includes a microchannel flow channel 201a. The microchannel flow channel 201a cross section aspect ratio, width and depth, is sized to prevent the sample 202 and magnetic nanoparticles 202a (or magnetic polystyrene-coated beads) from vertical stacking.

A carrier fluid source 203 introduces a carrier fluid 203a through a connecting channel 204 into the flow channel 201a. The connecting channel 204 meets the flow channel 201a at the junction 206. The carrier fluid 203 can be air, water, oil, fluorocarbon-based fluid, or other carrier fluid. Magnetic particles 202a are associated with the sample 202. The sample 202 to be analyzed together with associated magnetic particles 202a (or polystyrene beads) are introduced to the channel 204. The sample 202 can be bacterial cells, virus particles, nucleic acids, proteins, biomolecules, chemical agents, explosives agents, or other targets of interest. The flow channel 201a carries the sample 202 to be analyzed together with the associated magnetic particles 202a. For example, the flow channel 201a can carry genomic viral, bacterial, plant, animal, or human nucleic acid hybridized to magnetic-cored nanoparticles 202a (or polystyrene beads).

The sample 202 to be analyzed together with the associated magnetic particles 202a are carried to a capture zone 212 by the carrier fluid 203. The sample 202 to be analyzed together with the associated magnetic particles 202a are trapped in the capture zone 210 by activation of electromagnets 207. The sample 202 to be analyzed together with the associated magnetic particles 202a are captured in the magnetic and fluidic trap (capture zone) 210 using the Electro magnets 107.

An analyzer system provides analysis of the sample 202. Various kinds of analysis can be provided by the analyzer system For example, the analyzer system can provide optical excitation by LED, laser, or other means 208 that will elicit the strongest response, and the analyzer system will capture this signal at such sensors as a photodiode with trans-impedance amplifier, or an imaging array such as a CCD or CMOS imager 209. The empty droplets are directed out of the system as indicated by the arrow 211.

Sample washing and reagent replacement or refresh can be performed with this system 200. The target molecules 202, attached to the magnetic beads 202a and held in the detection zone 210, can be washed by the continuous flow of the channel 201a which, with upstream valving, can bring new and different reagents for multi-step reactions, or change the buffered pH to improve the optical efficiency of the fluorescing probe. For reagent sequencing, this system allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" 210 by electromagnetic attraction.

Referring again to FIG. 2, the operation of the system 200 will be described. Aqueous fluid 203 containing magnetic nanoparticles or magnetic polystyrene-coated beads 202a is introduced into the channel 201a. The carrier fluid 203 can be air, water, oil, fluorocarbon-based fluid, or other carrier fluid. The reactions using catalyzed and buffered reagents within the aqueous stream can be used as desired. The sample 202 pass into the "Capture Zone" 210 and the electromagnets 207 are activated to capture the magnetic nanoparticles or magnetic polystyrene-coated beads 202a and the sample 202.

Various analysis can be performed on the sample 202. For example, in one embodiment, when the sample 202 pass through the "Capture Zone" 210, the electromagnets 207 strip the passing droplets 205 of their nanoparticles 202a, accumulating them first near the walls (close to the magnets 207) and then further and further into the free stream of the fluid flow. As the entire channel begins to fill, optical density reaches a practical maximum, and the nanoparticles 202a are excited by laser or LED light source 208 into fluorescence. As they fluoresce, their emission is read by a photodiode with amplification (such as a Trans-impedance amplifier), or an imaging system such as a CCD or CMOS array 209. After the measurement is taken, the magnets 207 are de-energized and the magnetic beads, or nanoparticles, wash away, clearing the channel for the next assay.

Alternate embodiments utilize the same method applied to aqueous flows under Poiseiulle (parabolic) profiles, electrophoretic flows, segmented slug flows (aqueous with gas pockets), and others. Each requires simply a tuning of the magnetic force applied to capture and hold the magnetic nanoparticles.

Figure 3:
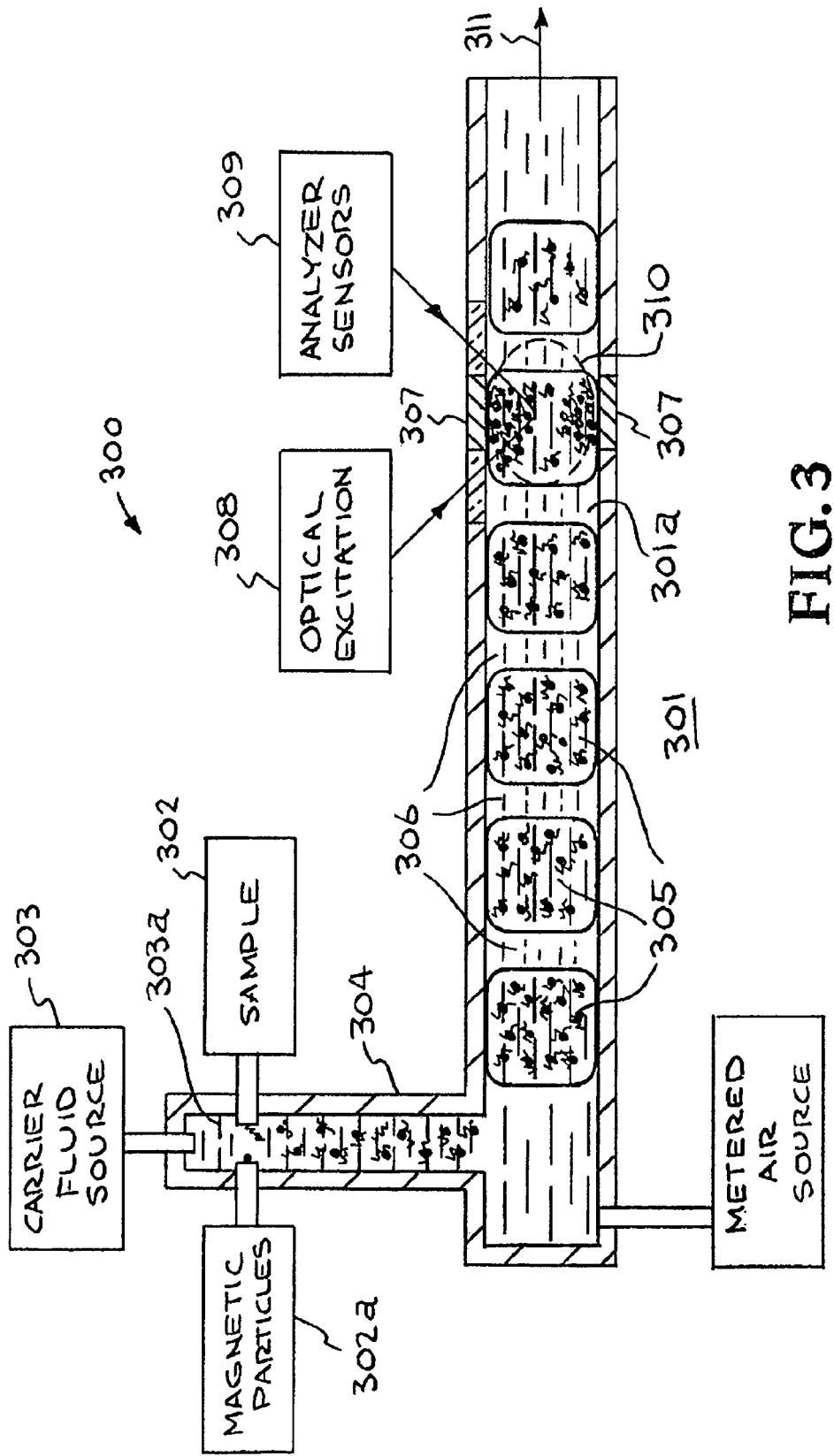
FIG. 3 illustrates yet another embodiment of a system for analyzing a sample constructed in accordance with the present invention.

Referring now to FIG. 3, yet another embodiment of a system for analyzing a sample constructed in accordance with the present invention is illustrated. The system is designated generally by the reference numeral 300. The system 300 provides analysis of a sample 302 on a microchip 301. The microchip 301 includes a microchannel flow channel 301a. The microchannel flow channel 301a cross section aspect ratio, width and depth, is sized to prevent the sample 302 and magnetic nanoparticles 302a (or magnetic polystyrene-coated beads) from vertical stacking.

A carrier fluid source 303 introduces a carrier fluid 303a through a connecting channel 304 into the flow channel 301a. The carrier fluid 303a can be air, water, oil, fluorocarbon-based fluid, or other carrier fluid. Magnetic particles 302a are associated with the sample 302. The sample 302 to be analyzed together with associated magnetic particles 302a (or polystyrene beads) are introduced to the channel 304. The sample 302 can be bacterial cells, virus particles, nucleic acids, proteins, biomolecules, chemical agents, explosives agents, or other targets of interest. The flow channel 301a carries the sample 302 to be analyzed together with the associated magnetic particles 302a. For example, the flow channel 301a can carry genomic viral, bacterial, plant, animal, or human nucleic acid hybridized to magnetic-cored nanoparticles 302a (or polystyrene beads).

The flow of carrier fluid 303a occurs in channel 301a separated into liquid slugs 305 metered by air into air sections 306. The carrier fluid source 303 includes a system for pulsing air into the carrier fluid 303a to form the liquid slugs 305. The sample 302 to be analyzed together with the associated magnetic particles 302a are carried to a capture zone 312 by the carrier fluid 303a. The sample 302 to be analyzed together with the associated magnetic particles 302a are trapped in the capture zone 310 by activation of electromagnets 307. The sample 302 to be analyzed together with the associated magnetic particles 302a are captured in the magnetic and fluidic trap (capture zone) 310 using the electro magnets 307.

An analyzer system provides analysis of the sample 302. Various kinds of analysis can be provided by the analyzer system For example, the analyzer system can provide optical excitation by LED, laser, or other means 308 that will elicit the strongest response, and the analyzer system will capture this signal at such sensors as a photodiode with trans-impedance amplifier, or an imaging array such as a CCD or CMOS imager 309. The empty droplets are directed out of the system as indicated by the arrow 311.

Sample washing and reagent replacement or refresh can be performed with this system 300. The target molecules 302, attached to the magnetic beads 302a and held in the detection zone 310, can be washed by the continuous flow of the channel 301a which, with upstream valving, can bring new and different reagents for multi-step reactions, or change the buffered pH to improve the optical efficiency of the fluorescing probe. For reagent sequencing, this system allows multistep reactions where one reagent "cocktail" can be washed over the magnetic beads, allowed to mix, and then washed away with pure buffer, and the process can continue with the next step. Also, with convective or diffusive heating such as from surface resistors within the channel, the temperature, pH, and flow rate can be tailored to each reaction step, thus optimizing overall efficiency and yield.

Similarly, this provides a method for studying the real-time performance of different fluorescing probes on the pH of the buffer, or on molecular concentration in the solvent. In this case the pH can sweep from one limit to another by changing the pH of the flow at the channel inlet, while the optical detection system reads the fluorescing probes which are held captive in the "Capture Zone" 310 by electromagnetic attraction.

Referring again to FIG. 3, the operation of the system 300 will be described. Aqueous fluid 303a containing magnetic nanoparticles or magnetic polystyrene-coated beads 302a is introduced into the channel 301a. The carrier fluid 303a can be air, water, oil, fluorocarbon-based fluid, or other carrier fluid. The reactions using catalyzed and buffered reagents within the aqueous stream can be used as desired. The sample 302 pass into the "Capture Zone" 310 and the electromagnets 307 are activated to capture the magnetic nanoparticles or magnetic polystyrene-coated beads 302a and the sample 302.

Various analysis can be performed on the sample 302. For example, in one embodiment, when the sample 302 pass through the "Capture Zone" 310, the electromagnets strip 307 the passing sample of their nanoparticles 302a, accumulating them first near the walls (close to the magnets 307) and then further and further into the free stream of the fluid flow. As the entire channel begins to fill, optical density reaches a practical maximum, and the nanoparticles 302a are excited by laser or LED light source 308 into fluorescence. As they fluoresce, their emission is read by a photodiode with amplification (such as a Trans-impedance amplifier), or an imaging system such as a CCD or CMOS array 309. After the measurement is taken, the magnets 307 are de-energized and the magnetic beads, or nanoparticles, wash away, clearing the channel for the next assay.

Alternate embodiments utilize the same method applied to aqueous flows under Poiseiulle (parabolic) profiles, electrophoretic flows, segmented slug flows (aqueous with gas pockets), and others. Each requires simply a tuning of the magnetic force applied to capture and hold the magnetic nanoparticles.

Figure 4:
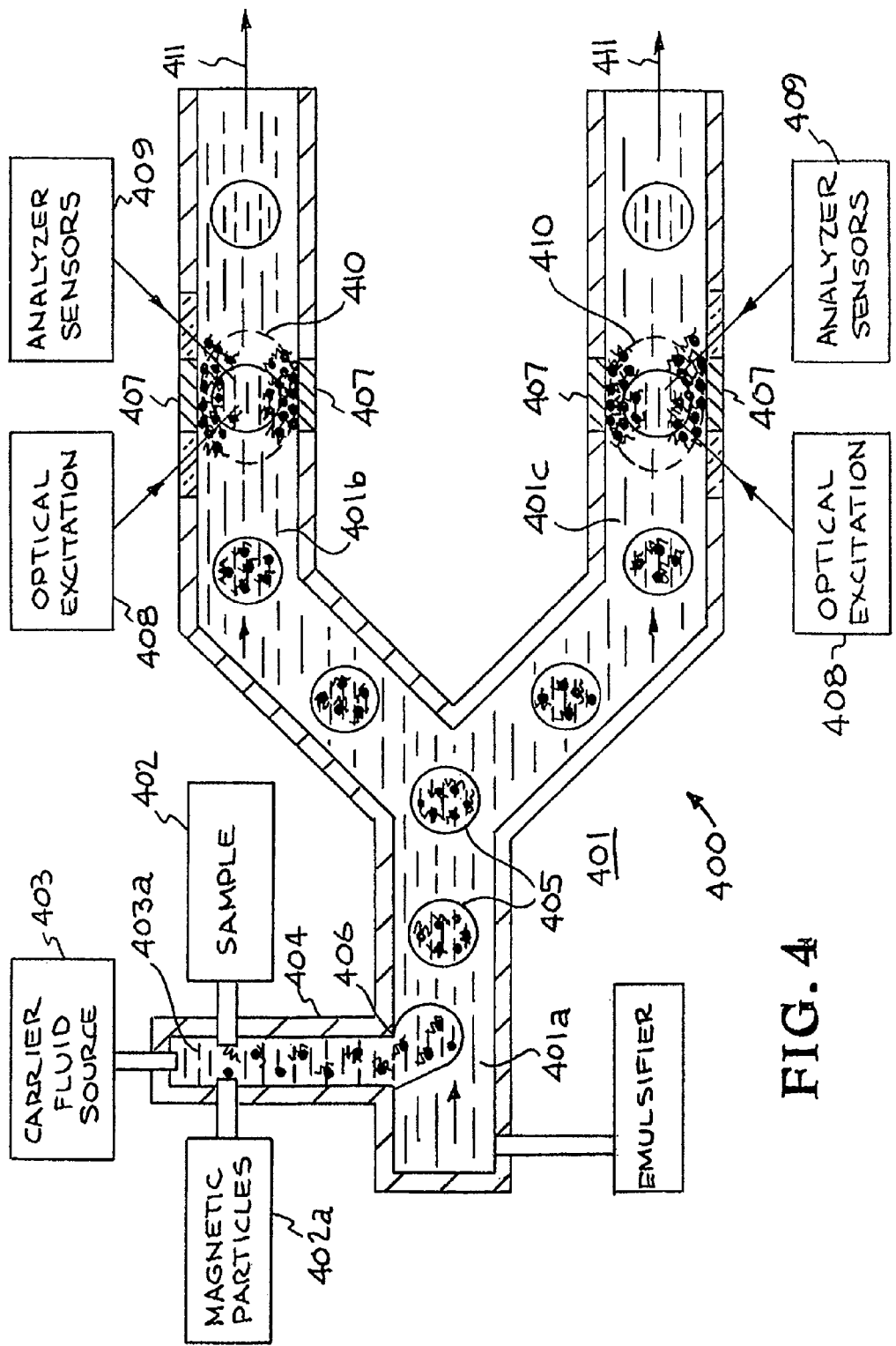
FIG. 4 illustrates another embodiment of a system for analyzing a sample constructed in accordance with the present invention.

Referring now to the drawings and in particular to FIG. 4, another embodiment of a system for analyzing a sample constructed in accordance with the present invention is illustrated. The system is designated generally by the reference numeral 400. The system 400 includes a microfluidic network of parallel or branched microchannels.

The system 400 provides analyzing a sample on a microchip 401. The microchip 401 includes a microchannel flow channel 401a and a microfluidic network of parallel or branched microchannels 401b and 401c. A carrier fluid source 403 introduces a carrier fluid 403a through a connecting channel 404 into the flow channel 401a. The sample 402 to be analyzed together with suspended magnetic particles 402a is introduced to the channel 404. The sample 402 can be bacterial cells, virus particles, nucleic acids, proteins, biomolecules, chemical agents, explosives agents, and other targets of interest. A droplet maker 406 is connected to the channel 404 and flow channel 401a and produces droplets 405 containing the sample 402 and the magnetic particles 402a.

The flow channel 401a can carry genomic viral, bacterial, plant, animal, or human nucleic acid hybridized to magnetic-cored nanoparticles 402a (or polystyrene beads). The microchannel flow channel 401a cross section aspect ratio, width and depth, is sized to prevent the sample 402 and magnetic nanoparticles 402a (or magnetic polystyrene-coated beads) from vertical stacking.

The droplets or microreactors 405 containing the sample 402 with magnetic particles 402a are carried to a capture zone 410 in the microfluidic network of parallel or branched microchannels 401b by the carrier fluid 403. The droplets or microreactors 405 containing the sample 402 with magnetic particles 402a are trapped in the capture zone 410 by activation of electromagnets 407. The drops (isolated mobile reactors) 405 with their suspended magnetic particles 402a are captured in the magnetic and fluidic trap (capture zone) 410 using the electro magnets 407.

An analyzer system provides analysis of the sample 402. The analyzer system provides optical excitation by LED, laser, or other means 408 that will elicit the strongest response, and the analyzer system will capture this signal at such sensors as a photodiode with trans-impedance amplifier, or an imaging array such as a CCD or CMOS imager 409. The empty droplets are directed out of the system as indicated by the arrow 411.

Referring again to FIG. 4, the operation of the system 400 will be described. Aqueous fluid 402 containing magnetic nanoparticles 402a is injected into a cross-channel flow of oil (or other carrier fluid) carrier fluid 403. The reactions between the hybridized molecules on the magnetic nanoparticle 402a and the catalyzed and buffered reagents within the aqueous stream occur, powered by the addition of heat or light into the channel if necessary. When the droplets 405 pass through the optical enhancement, or "Capture Zone" 410 in the microfluidic network of parallel or branched microchannels 401b, the electromagnets strip 407 the passing droplets 405 of their nanoparticles 402a, accumulating them first near the walls (close to the magnets 407) and then further and further into the free stream of the fluid flow. As the entire channel begins to fill, optical density reaches a practical maximum, and the nanoparticles 402a are excited by laser or LED light source 408 into fluorescence. As they fluoresce, their emission is read by a photodiode with amplification (such as a Trans-impedance amplifier), or an imaging system such as a CCD or CMOS array 409. After the measurement is taken, the magnets 407 are de-energized and the magnetic beads, or nanoparticles, wash away, clearing the channel for the next assay. Some of the advantages and results (unexpected) produced by the system 400 include the fact that the system 400 and other embodiments with additional branches provide higher throughput. The system 400 and other embodiments with additional branches can process a larger volume of sample. The system 400 and other embodiments with additional branches can process a fixed volume of sample at faster rate.

The systems 100, 200, 300, and 400 provide other unexpected and improved results. The article "On-Chip, Real-Time, Single-Copy Polymerase Chain Reaction in Picoliter Droplets," by N. Reginald Beer, Benjamin J. Hindson, Elizabeth K. Wheeler, Sara B. Hall, Klint A. Rose, Ian M. Kennedy, and Bill W. Colston; in *Analytical Chemistry*, Vol. 79, No. 22: Nov. 15, 2007 shows that some portions or all of the systems 100, 200, 300, and 400 were tested and analyzed. The article "On-Chip, Real-Time, Single-Copy Polymerase Chain Reaction in Picoliter Droplets," by N. Reginald Beer, Benjamin J. Hindson, Elizabeth K. Wheeler, Sara B. Hall, Klint A. Rose, Ian M. Kennedy, and Bill W. Colston; in *Analytical Chemistry*, Vol. 79, No. 22: Nov. 15, 2007 is incorporated herein by this reference. The article "New system detects small samples for big gains" in NewsLine, Vol. 32, No. 39, Nov. 16, 2007, also shows that some portions or all of the systems 100, 200, 300, and 400 were tested and analyzed. The article "New system detects small samples for big gains" in NewsLine, Vol. 32, No. 39, Nov. 16, 2007 is incorporated herein by this reference.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for analysis of a sample, comprising:
a microchip,
a microchannel flow channel in said microchip,
a connecting channel connected to said microchannel flow channel,
a source of magnetic particles that produces magnetic particles, said source of magnetic particles connected to said connecting channel wherein said source of magnetic particles delivers said magnetic particles to said connecting channel,
a source of carrier fluid connected to said connecting channel for moving the sample in said connecting channel,
a source of the sample connected to said connecting channel,
fluorescent probes associated with said magnetic particles, said carrier fluid, and said sample,
a source of microchannel flow channel carrier fluid connected to said microchannel flow channel wherein said microchannel flow channel carrier fluid is positioned to move the sample, said magnetic particles, and said fluorescent probes from said connecting channel into said microchannel flow channel and to move the sample, said magnetic particles, and said fluorescent probes in the microchannel flow channel, an electromagnet trap connected to said microchannel flow channel for selectively magnetically trapping the sample, said magnetic particles, and said fluorescent probes, and an analyzer positioned at or proximate said electromagnet trap for detecting said fluorescent probes and analyzing the sample.

2. The apparatus for analysis of a sample of claim 1 further comprising a droplet maker connected to said microchannel flow channel for producing droplets containing the sample, said fluorescent probes, and said magnetic particles.

3. The apparatus for analysis of a sample of claim 1 further comprising a system for producing liquid slugs in said microchannel flow channel with said liquid slugs containing the sample, said fluorescent probes, and said magnetic particles.

4. The apparatus for analysis of a sample of claim 1 wherein said flow channel in said microchip has a cross section aspect ratio, width and depth, that is sized to prevent said magnetic particles from vertical stacking.

5. The apparatus for analysis of a sample of claim 1 wherein said electromagnet trap is a microfluidic network of parallel or branched microchannels.

6. The apparatus for analysis of a sample of claim 1 wherein said source of carrier fluid is a source of oil connected to said flow channel.

7. The apparatus for analysis of a sample of claim 1 wherein said source of carrier fluid is a source of fluorocarbon-based fluid carrier fluid connected to said flow channel.

8. The apparatus for analysis of a sample of claim 1 wherein said magnetic particles are magnetic-cored optically discrete nanoparticles.

9. The apparatus for analysis of a sample of claim 1 wherein said magnetic particles are magnetic polystyrene-coated beads.

10. The apparatus for analysis of a sample of claim 1 wherein said analyzer includes a photodiode.

11. The apparatus for analysis of a sample of claim 1 wherein said analyzer includes a CCD or CMOS array.

12. The apparatus for analysis of a sample of claim 1 wherein said analyzer includes a laser.

13. The apparatus for analysis of a sample of claim 1 wherein said analyzer includes a LED light source.

14. The apparatus for analysis of a sample of claim 1 wherein said electromagnet trap includes an electromagnet.

15. An apparatus for analysis of a sample comprising:
a microchip,
a microchannel flow channel in said microchip,
a connecting channel connected to said microchannel flow channel,
a source of magnetic particles connected to said connecting channel that delivers said magnetic particles to said connecting channel,
a source of carrier fluid connected to said connecting channel for moving the sample in said connecting channel,
a source of the sample connected to said connecting channel,
fluorescence probes associated with said magnetic particles, said carrier fluid, and said sample,
a pulsed source of carrier fluid connected to said flow channel that pulses carrier fluid into said flow channel and creates liquid slugs in said flow channel containing the sample, said magnetic particles, and said fluorescent probes, an electromagnet trap connected to said flow channel for selectively magnetically trapping said liquid slugs containing the sample, said magnetic particles, and said fluorescent probes, and an analyzer positioned at or proximate said electromagnet trap for detecting said fluorescent probes and analyzing the sample.

16. An apparatus for analysis of a sample, comprising:
a microchip,
a microchannel flow channel in said microchip,
a connecting channel connected to said microchannel flow channel,
a source of magnetic particles connected to said connecting channel that delivers said magnetic particles to said connecting channel,
a source of carrier fluid connected to said connecting channel for moving the sample in said connecting channel,
a source of the sample connected to said connecting channel,
fluorescent probes associated with said magnetic articles said carrier fluid, and said sample,
a droplet maker connected to said flow channel for producing droplets containing the sample, said fluorescent probes, and said magnetic particles,
an electromagnet trap connected to said flow channel for selectively magnetically trapping said droplets containing the sample, said fluorescent probes, and said magnetic particles, and
an analyzer positioned at or proximate said electromagnet trap for detecting said fluorescent probes and analyzing the sample.

17. The apparatus for analysis of a sample of claim 16 wherein said microchannel flow channel in said microchip has a cross section aspect ratio, width and depth, that is sized to prevent said magnetic particles from vertical stacking.

18. A method of analyzing a sample on a microchip, comprising the steps of:
providing a microchannel flow channel in the microchip;
providing a connecting channel connected to said microchannel flow channel,
providing a source of carrier fluid connected to said connecting channel for moving the sample in said connecting channel,
providing a source of the sample connected to said connecting channel,
providing a source of magnetic nanoparticles or magnetic polystyrene-coated beads connected to said connecting channel,
providing fluorescent probes associated with the sample, with said carrier fluid, and with said magnetic nanoparticles or magnetic polystyrene-coated beads;
moving the sample with said fluorescent probes and said magnetic nanoparticles or magnetic polystyrene-coated beads in said connecting channel into said microchannel flow channel and in said microchannel flow channel,
trapping the sample with said fluorescent probes and said magnetic nanoparticles or magnetic polystyrene-coated beads in a magnetic trap in said microchannel flow channel, and
providing an analyzer positioned at or proximate said electromagnet trap for detecting said fluorescent probes and analyzing the sample.

19. The method of analyzing a sample on a microchip of claim 18 further comprising the step of forming microreactor droplets in said microchannel flow channel, said microreactor droplets containing the sample, said fluorescent probes, and said magnetic nanoparticles or magnetic polystyrene-coated beads.

20. The method of analyzing a sample on a microchip of claim 18 further comprising the step of forming liquid slugs in said microchannel flow channel, said liquid slugs containing the sample, said fluorescent probes, and said magnetic nanoparticles or magnetic polystyrene-coated beads.

21. The method of analyzing a sample on a microchip of claim 18 wherein said step of providing a source of magnetic nanoparticles or magnetic polystyrene-coated beads connected to said connecting channel comprises providing a source of magnetic nanoparticles connected to said connecting channel.

22. The method of analyzing a sample on a microchip of claim 18 wherein said step of providing a source of magnetic nanoparticles or magnetic polystyrene-coated beads connected to said connecting channel comprises providing a source of magnetic-cored optically discrete nanoparticles connected to said connecting channel.

23. The method of analyzing a sample on a microchip of claim 18 wherein said step of providing a source of magnetic nanoparticles or magnetic polystyrene-coated beads connected to said connecting channel comprises providing a source of magnetic polystyrene-coated beads connected to said connecting channel.

24. The method of analyzing a sample on a microchip of claim 18 wherein said step of providing a microchannel flow channel in the microchip comprises providing a microchannel flow channel cross section aspect ratio, width and depth, that prevents said magnetic nanoparticles or magnetic polystyrene-coated beads from vertical stacking.

25. The method of analyzing a sample on a microchip of claim 18 further comprising the step of flowing reagent over and through the sample and said magnetic nanoparticles or magnetic polystyrene-coated beads in said magnetic trap.

26. A method of analyzing a sample, comprising the steps of:
providing a microchannel flow channel;
providing a connecting channel connected to said microchannel flow channel,
providing a source of carrier fluid connected to said connecting channel for moving the sample in said connecting channel,
providing a source of the sample connected to said connecting channel,
providing a source of magnetic nanoparticles or magnetic polystyrene-coated beads connected to said connecting channel,
providing fluorescent probes associated with the sample, with said carrier fluid, and with said magnetic nanoparticles or magnetic polystyrene-coated beads;
providing a droplet maker connected to said connecting channel and to said flow channel for producing droplets containing the sample, said fluorescent probes, and said magnetic nanoparticles or magnetic polystyrene-coated beads,
moving said droplets with the sample, with said fluorescent probes, and with said magnetic nanoparticles or magnetic polystyrene-coated beads in said microchannel flow channel;
holding said droplets with the sample, with said fluorescent probes, and with said magnetic nanoparticles or magnetic polystyrene-coated beads in a magnetic trap in said microchannel flow channel; and
providing an analyzer positioned at or proximate said electromagnet trap for detecting said fluorescent probes and analyzing the sample obtaining an enhanced analysis signal.

27. The method of analyzing a sample of claim 26 further comprising the step of holding the sample, said fluorescent probes, and said magnetic nanoparticles or magnetic polystyrene-coated beads in said magnetic trap in said microchannel flow channel while washing the sample or exposing the sample to reagents or exposing the sample to other conditions.

* * * * *